US008874236B2

(12) United States Patent
Liu et al.

(10) Patent No.: US 8,874,236 B2
(45) Date of Patent: Oct. 28, 2014

(54) ELECTRONIC PACEMAKER AND PACEMAKER LEAD

(75) Inventors: Kai Liu, Beijing (CN); Li Fan, Beijing (CN); Ying-Hui Sun, Beijing (CN); Wen-Mei Zhao, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/096,209

(22) Filed: Apr. 28, 2011

(65) Prior Publication Data

US 2012/0004702 A1    Jan. 5, 2012

(30) Foreign Application Priority Data

Jul. 5, 2010   (CN) .......................... 2010 1 0217663

(51) Int. Cl.
*A61N 1/00* (2006.01)
*A61N 1/05* (2006.01)
*B82Y 30/00* (2011.01)

(52) U.S. Cl.
CPC ............... *A61N 1/0529* (2013.01); *B82Y 30/00* (2013.01)
USPC ...................................................... 607/119

(58) Field of Classification Search
CPC ....................................................... A61N 1/056
USPC .................................................. 607/116–156
See application file for complete search history.

(56) References Cited

U.S. PATENT DOCUMENTS

| 7,354,877 | B2 * | 4/2008 | Rosenberger et al. | ........ 442/194 |
| 7,894,914 | B2 * | 2/2011 | Stahmann et al. | ............ 607/119 |
| 2007/0293086 | A1 | 12/2007 | Liu et al. | |
| 2008/0161886 | A1 | 7/2008 | Stevenson et al. | |
| 2008/0170982 | A1 | 7/2008 | Zhang et al. | |
| 2009/0062895 | A1 | 3/2009 | Stahmann et al. | |
| 2009/0202764 | A1 * | 8/2009 | Tonon et al. | ................. 428/36.3 |
| 2009/0255706 | A1 | 10/2009 | Jiang et al. | |
| 2009/0278436 | A1 | 11/2009 | Xiao et al. | |
| 2010/0057157 | A1 | 3/2010 | Govari et al. | |

FOREIGN PATENT DOCUMENTS

| CN | 2734251 | 10/2005 |
| CN | 1943813 A | 4/2007 |
| CN | 101090011 | 12/2007 |
| CN | 101576423 | 11/2009 |
| CN | 101676004 A | 3/2010 |
| JP | 2008-523254 | 7/2008 |
| JP | 2009-29218 | 2/2009 |
| JP | 2009-65171 | 3/2009 |
| JP | 2009-137722 | 6/2009 |
| JP | 2010-55421 | 3/2010 |
| TW | 200945372 A | 11/2009 |
| WO | WO2009065171 | 5/2009 |
| WO | WO2010055421 | 5/2010 |

* cited by examiner

*Primary Examiner* — Christopher D Koharski
*Assistant Examiner* — Nadia Mahmood
(74) *Attorney, Agent, or Firm* — Novak Druce Connolly Bove + Quigg LLP

(57) ABSTRACT

A pacemaker lead includes a body and an insulation layer. The body includes at least one carbon nanotube yarn. The at least one carbon nanotube yarn includes a plurality of carbon nanotubes. The carbon nanotubes are interconnected along an axis of the body by van der Waals force. The insulation layer covers an outer surface of the body.

20 Claims, 4 Drawing Sheets

ELECTRONIC PACEMAKER AND PACEMAKER LEAD

BACKGROUND

1. Technical Field

The present application is related to electronic pacemakers, and more particularly to a pacemaker and a pacemaker lead, which uses carbon nanotubes.

2. Description of Related Art

Parkinson's disease (PD) is a degenerative disorder of the central nervous system that impairs motor skills, cognitive processes, and other functions. PD is the most common cause of chronic progressive syndrome characterized by tremor, rigidity, bradykinesia, and postural instability.

Deep brain stimulation (DBS) is presently the most used surgical means of treatment but other surgical therapies consisting of producing lesions in specific subcortical areas are also effective. DBS involves the implantation of a medical device called a brain pacemaker, which sends electrical impulses to specific parts of the brain.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Reference will now be made to the drawings to describe various inventive embodiments of the present disclosure in detail, wherein like numerals refer to like elements throughout.

Figure 1:
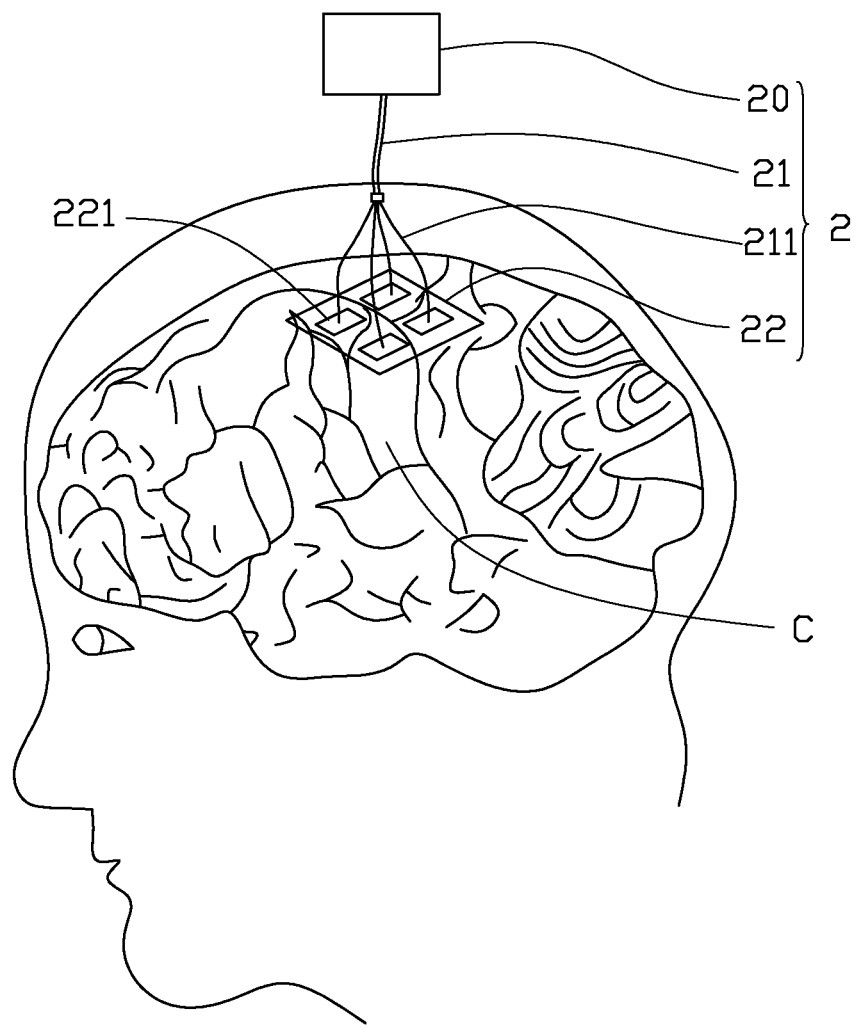
FIG. 1 is a diagram of an electronic pacemaker according to a first embodiment of the disclosure.
Figure 2:
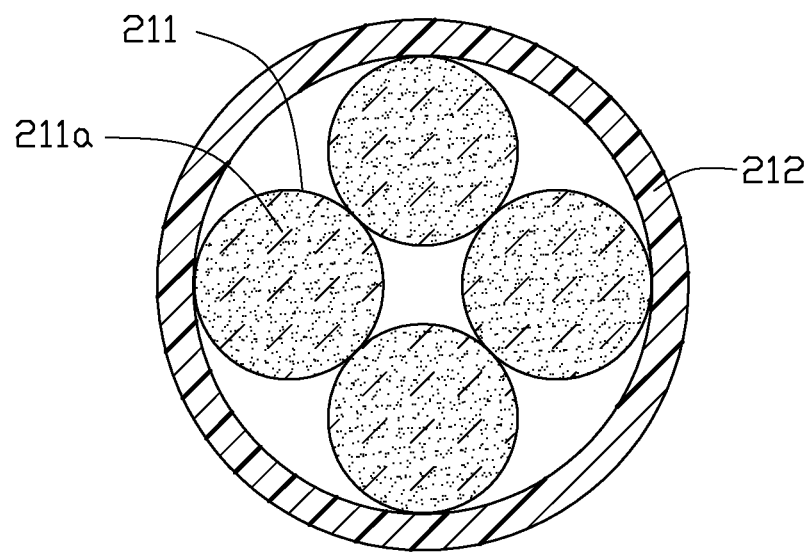
FIG. 2 is a diagram of a pacemaker lead of the electronic pacemaker electrode of FIG. 1.

Referring to FIG. 1 and FIG. 2, a pacemaker 2 according to an embodiment of the disclosure includes a pulsed current generator 20, a pacemaker lead 21, and an electrode member 22. In the embodiment, the pacemaker 2 can be a brain pacemaker.

The pulsed current generator 20 generates a current for stimulating the target cells, for example, the cerebral cells C. In the embodiment, the current is a pulsed current with a modulated pulse width.

The pacemaker lead 21 has at least one body 211 and an insulation layer 212, which covers the body 211 (shown in FIG. 2). The pacemaker lead 21 is connected to the pulsed current generator 20 for transmitting the current. In the embodiment, the pacemaker lead 21 has a plurality of bodies 211 covered by the insulation layer 212. The material of the insulation layer 212 may be a high polymer material like polyurethane, and the thickness of the insulation layer 212 is in the range from about 1 μm to about 50 μm.

Referring to FIG. 1 again, the electrode member 22 is connected to the pacemaker lead 21 and contacts the cerebral cells C. The electrode member 22 has a plurality of terminals 221 corresponding to the body 211 of the pacemaker lead 21. The terminals 221 are arranged in an electrode array to stimulate the cerebral cells C at different positions simultaneously. In the embodiment, the terminal 221 is a metal terminal having a strip or a cone shape.

Figure 3:
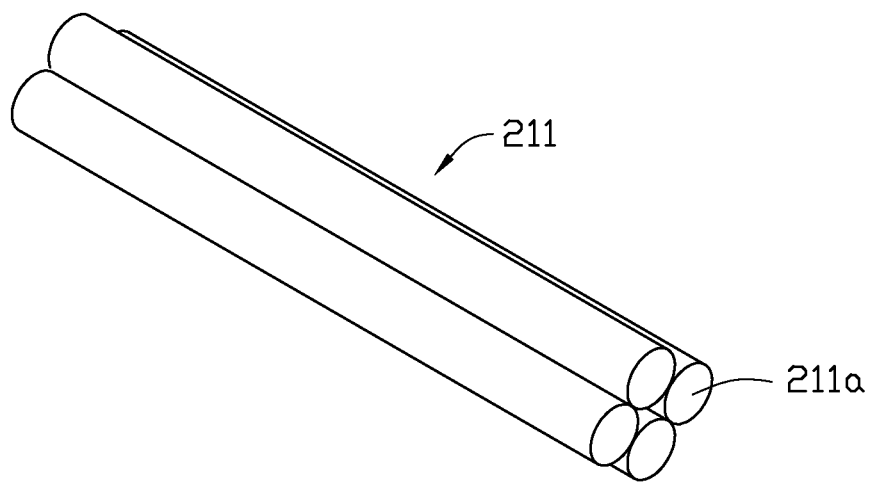
FIG. 3 is a diagram of a number of carbon nanotube yarns arranged to contact with each other to form a bundle structure.
Figure 4:
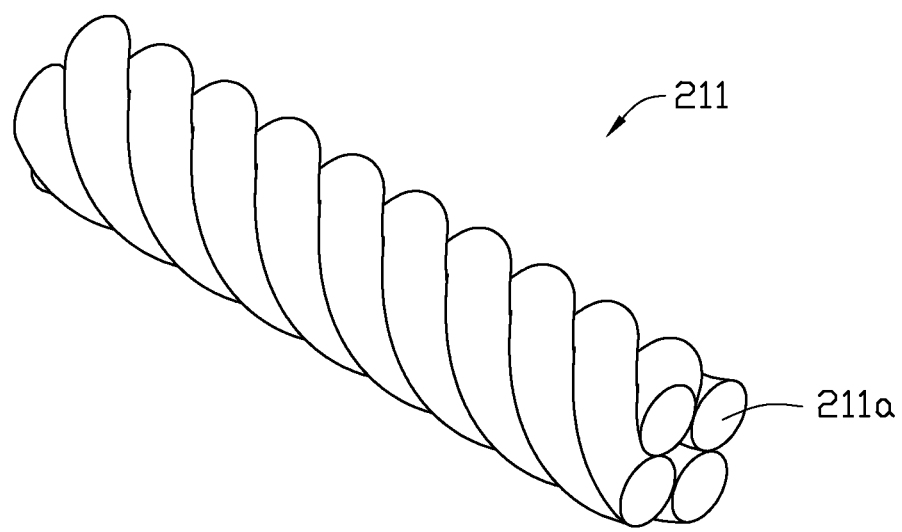
FIG. 4 is a diagram of a number of carbon nanotube yarns wound to form a bundle structure.

Referring also to FIG. 3 and FIG. 4, the body 211 is a linear structure and includes at least one carbon nanotube yarn 211a. The diameter of the carbon nanotube yarn 211a is in the range from about 1 μm to about 100 μm, and the diameter of the body 211 is in the range from about 1 μm to about 1 mm. In the embodiment, the body 211 has a plurality of carbon nanotube yarns 211a, and each one of the carbon nanotube yarns 211a includes a plurality of carbon nanotubes, which are interconnected to each other along one axis of the body 211 by van der Waals force and have almost the same length (not shown in FIG.). In the embodiment, the carbon nanotubes can be single-walled carbon nanotubes or multi-walled carbon nanotubes.

FIG. 3 is a diagram showing the carbon nanotube yarns 211a arranged tightly contacting each other in parallel to form a bundle structure. FIG. 4 is a diagram showing the carbon nanotube yarns 211a spirally wound around the axis of the body 211 at zero pitch to form the bundle structure.

In the embodiment, the carbon nanotubes are connected by covalent bonds so the carbon nanotube yarn has characteristics like high toughness or high resilience. The carbon nanotube structures described herein can be used in a similar manner for other parts in other kinds of pacemakers such as artificial pacemakers used for the heart.

It is to be understood, however, that even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

What is claimed is:

1. A pacemaker lead, comprising:
   a body comprising at least one carbon nanotube yarn, which comprises a plurality of carbon nanotubes interconnected along an axis of the body by van der Waals force; and
   an insulation layer covering an outer surface of the at least one carbon nanotube yarn close to a target cell,
   wherein the pacemaker lead transmits a current for stimulating the target cell.

2. The pacemaker lead of claim 1, wherein the plurality of carbon nanotubes have almost the same length.

3. The pacemaker lead of claim 1, wherein the plurality of carbon nanotubes are arranged in parallel according to the axis of the body.

4. The pacemaker lead of claim 1, wherein the plurality of carbon nanotubes are wound along the axis of the body.

5. The pacemaker lead of claim 1, wherein a diameter of the plurality of carbon nanotube yarn is in a range from about 1 μm to about 100 μm.

6. The pacemaker lead of claim 1, wherein a thickness of the insulation layer is in a range from about 1 μm to about 50 μm.

7. The pacemaker lead of claim 1, wherein the body comprises at least two carbon nanotube yarns wound around the axis of the body.

8. The pacemaker lead of claim 1, wherein the plurality of carbon nanotubes are single-walled carbon nanotubes or multi-walled carbon nanotubes.

9. A pacemaker, comprising:
a pulsed current generator generating a current for stimulating a target cell;
a plurality of pacemaker leads connected to the pulsed current generator and transmitting the current, and each pacemaker lead comprising:
a body comprising at least one carbon nanotube yarn comprising a plurality of carbon nanotubes interconnected along an axis of the body by van der Waals force; and
an insulation layer covering an entire outer surface of the at least one carbon nanotube yarn close to the target cell; and
an electrode member comprising a plurality of terminals arranged in an electrode array, wherein each pacemaker lead is corresponding to the plurality of terminals.

10. The pacemaker of claim 9, wherein the plurality of terminals are made of metal.

11. The pacemaker of claim 9, wherein the plurality of carbon nanotubes have almost the same length.

12. The pacemaker of claim 9, wherein the plurality of carbon nanotubes are arranged in parallel according to the axis of the body.

13. The pacemaker of claim 9, wherein the plurality of carbon nanotubes are wound along the axis of the body.

14. The pacemaker of claim 9, wherein a diameter of the carbon nanotube yarn is in the range from about 1 µm to about 100 µm.

15. The pacemaker of claim 9, wherein a thickness of the insulation layer is in the range from about 1 µm to about 50 µm.

16. The pacemaker of claim 9, wherein the body comprises at least two carbon nanotube yarns wound around the axis of the body.

17. The pacemaker of claim 9, wherein the plurality of carbon nanotubes are single-walled carbon nanotubes or multi-walled carbon nanotubes.

18. The pacemaker of claim 9, wherein the plurality of pacemaker leads are wound to each other at zero torque pitch.

19. A pacemaker lead for a pacemaker, the pacemaker lead comprising:
a body consisting of at least one carbon nanotube yarn comprising a plurality of carbon nanotubes interconnected along an axis of the body by van der Waals force; and
an insulation layer surrounding an outer surface of the body close to cells,
wherein the at least one carbon nanotube yarn is configured to electrically connect to a pulse generator of the pacemaker and an electrode member of the pacemaker contacting the cells, and transferring current form the pacemaker to the electrode member to stimulate the cells.

20. The pacemaker of claim 19, wherein the plurality of carbon nanotubes are substantially parallel to or spirally wound around the axis of the body.

* * * * *